United States Patent [19]

Suyama et al.

[11] Patent Number: 5,773,984
[45] Date of Patent: *Jun. 30, 1998

[54] METHOD OF INSPECTING ABNORMALITY OCCURRING INSIDE PIPE AND APPARATUS FOR PRACTICING THE METHOD

[75] Inventors: Kiichi Suyama, Yokohama; Hajime Furusawa, Tokyo; Yasuharu Hosohara; Takashi Kobori, both of Yokohama, all of Japan

[73] Assignee: Tokyo Gas Co., Ltd., Tokyo, Japan

[ * ] Notice: The term of this patent shall not extend beyond the expiration date of Pat. No. 5,612,625.

[21] Appl. No.: 585,979

[22] Filed: Jan. 12, 1996

Related U.S. Application Data

[63] Continuation of Ser. No. 231,556, Apr. 21, 1994, abandoned.

[30] Foreign Application Priority Data

Jun. 15, 1993 [JP] Japan ................................. 5-168550
Jun. 18, 1993 [JP] Japan ................................. 5-172231

[51] Int. Cl.$^6$ ..................................................... G01R 29/00
[52] U.S. Cl. ............................................................ 324/635
[58] Field of Search ............................. 73/627; 324/220, 324/326, 334, 639, 637, 635, 532, 642

[56] References Cited

U.S. PATENT DOCUMENTS

| 2,537,737 | 1/1951 | Chamberlin | 324/633 |
| 3,753,086 | 8/1973 | Shoemaker, Jr. | 324/523 |
| 3,990,003 | 11/1976 | Agee | 324/531 |
| 4,573,016 | 2/1986 | Nakamura et al. | 324/326 |
| 4,677,438 | 6/1987 | Michiguchi et al. | 324/337 |
| 5,019,822 | 5/1991 | Kirkland | 324/326 |
| 5,151,657 | 9/1992 | Tashjian | 324/326 |
| 5,194,812 | 3/1993 | Yokoi | 324/326 |
| 5,233,297 | 8/1993 | Lara | 324/220 |
| 5,373,443 | 12/1994 | Lee et al. | 324/338 |
| 5,408,182 | 4/1995 | Stolarczyk et al. | 324/338 |

FOREIGN PATENT DOCUMENTS

| 24 34 856 | 2/1976 | Germany . |
| 508635 | 8/1972 | U.S.S.R. . |

OTHER PUBLICATIONS

Patent Abstracts of Japan, vol. 16, No. 562 (P–1456) Dec. 3, 1991 & JP–A–04 215 046 (Nippon Steel Corp.) Aug. 5, 1992, Abstract.

Patent Abstracts of Japan, vol. 13, No. 508 (P–960) Nov. 15, 1989 & JP–A–01 206 246 (Osaka Gas Co. Ltd.) Abstract.

H. Mintrop, et al., "Die Anwendung von Mikrowellen zur Prüfung der Innengeometrie von schlanken Stahlrohren", in: Messen und Prüfen/Automatik, No. 10, Oct. 1973, pp. 635–637.

J.C. Gallop, et al., "Dimensional measurement by microwave resonances", in: E. Sci. Instrum. vol. 14, (1981), pp. 461–463.

J.C. Gallop, et al., "Shape and dimensional measurement using microwaves", in: J. Phys. E: Sci. Instrum. 19 (1986), pp. 413–417.

Primary Examiner—Christine K. Oda
Attorney, Agent, or Firm—Townsend and Townsend and Crew LLP

[57] ABSTRACT

A method of inspecting an abnormality occurring inside a pipe to be inspected, and an apparatus for practicing the method, which includes the steps of transmitting an electric radio or radio frequency (RF) wave having a predetermined frequency from an antenna of a transmitter located at a predetermined position inside the pipe, receiving the transmitted RF wave by an antenna of a receiver located at a predetermined position inside the pipe, and discriminating a characteristic of the received RF wave. The characteristic of the received RF wave can be the intensity of the RF wave, and an attenuation amount is detected in a first example. Alternatively, the characteristic of the received RF wave may be the time required to reflect the transmitted RF wave and receive it with the receiver, and the time interval between transmission of the RF wave and reception of the reflected RF wave is measured in this alternative.

5 Claims, 7 Drawing Sheets log MAG  10 dB/ REF −70 dB

START 1.0000 GHz         STOP 5.0000 GHz log MAG  10 dB/ REF−70 dB

START 1.0000 GHz         STOP 5.0000 GHz

| INTERNAL STATE OF PIPE | ATTENUATION AMOUNT OF RADIO FREQUENCY WAVE |
|---|---|
| FULL OPEN | -28.6 dbm |
| 1/3 CLOSED | -31.0 dbm |
| 1/2 CLOSED | -40.0 dbm |
| 2/3 CLOSED | -50.7 dbm |
| FULL CLOSE | -53.0 dbm |

…

METHOD OF INSPECTING ABNORMALITY OCCURRING INSIDE PIPE AND APPARATUS FOR PRACTICING THE METHOD

This is a Continuation of application Ser. No. 08/231,556, filed Apr. 21, 1994, now abandoned.

BACKGROUND OF THE INVENTION

1. Field of the Invention

The present invention relates to a method of inspecting abnormalities occurring inside a pipe such as a gas pipe buried underground, and an apparatus for practicing the method.

2. Description of the Relevant Arts

One known conventional method of inspecting whether a foreign substance such as earth and sand entered into a gas pipe or the like buried underground involves inserting an inspection camera into the pipe to pick up the internal state of the pipe and observe the resultant image, so that the presence/absence of an abnormality can be judged. In another method, a self-propelled robot is inserted into a pipe to inspect the internal state of the pipe (Japanese Patent Publication No. 59-147260). Further, a method of inserting a pig having an outer diameter almost equal to the inner diameter of a pipe to be inspected into the pipe is known. Still further, a method of sending a sound wave into a pipe to be inspected and receiving the reflected sound wave, thereby checking the internal state of the pipe (Japanese Patent Publication No. 51-18836) is known also.

In the above methods, however, when the camera, robot, and the like are used for inspecting the interior of a pipe, the pipe must not have a complicated bent shape. In addition, an access hole is required to insert the inspecting means. To prepare an access hole for buried pipe, cumbersome, time-consuming construction work such as digging must be performed. In addition, the inspection distance per cycle is limited to the length of an electric wire or the like connected to the robot or the like. For this reason, when the distance to be inspected is long, the number of inspection cycles are undesirably increased, thereby increasing cost. When a sound wave is sent into a pipe to inspect the internal state from the reflected sound wave, it is difficult to sense the internal state, except when the pipe is completely closed or open to air, and small changes cannot be detected.

SUMMARY OF THE INVENTION

The present invention has been made in consideration of the above situation, and has as a first object to provide a method of easily inspecting an abnormality occurring inside a pipe such as a gas pipe or the like buried underground, and an apparatus for practicing the method.

A second object of the present invention is to provide a method of easily and accurately detecting, as the intended target, the location of an abnormality inside the pipe, and an apparatus for practicing the method.

In order to achieve the above objects, according to a main aspect of the present invention, there is provided a method of inspecting an abnormality occurring inside a pipe to be inspected, comprising the steps of transmitting an electric radio or radio frequency ("RF") wave of a predetermined frequency from an antenna of a transmitter located at a predetermined position inside the pipe, receiving the transmitted RF wave with an antenna of a receiver located at a predetermined position inside the pipe, and discriminating a characteristic of the received RF wave.

In order to achieve the first named object, according to a second aspect of the present invention, there is provided a method of inspecting an abnormality occurring inside a pipe to be inspected, wherein the characteristic of the received RF wave to be discriminated is the intensity of the RF wave. An attenuation amount is detected by comparing the intensity of the received RF wave with the intensity of the transmitted RF wave. An abnormality which constricts an inner diameter of the pipe is judged to exist inside the pipe when the amount of attenuation of the received RF wave becomes more than a predetermined amount; i.e. exceeds a threshold level.

According to a third aspect of the present invention, there is provided a method of inspecting an abnormality occurring inside a pipe to be inspected when the transmitted RF wave is received by the antenna of the receiver spaced apart from the antenna of the transmitter by a predetermined distance inside the pipe.

According to a fourth aspect of the present invention, there is provided a method of inspecting an abnormality occurring inside a pipe to be inspected by changing the attenuation amount of the received RF wave as a function of the distance between the antenna of the transmitter and the antenna of the receiver.

Furthermore, in order to achieve the second object, according to a fifth aspect of the present invention, there is provided a method of inspecting an abnormality occurring inside a pipe to be inspected, wherein the characteristic of the received RF wave to be discriminated is the time required to reflect the transmitted RF wave being received by the receiver. The time interval between the transmission of the RF wave and its reception is measured and used to judge the abnormality inside the pipe and detect its position.

According to a sixth aspect of the present invention, there is provided a method of inspecting an abnormality occurring inside a pipe to be inspected wherein the transmitted RF wave is received by an antenna of a transceiver which functions both as a transmitter and a receiver.

According to a seventh aspect of the present invention, there is provided a method of inspecting an abnormality occurring inside a pipe to be inspected, wherein the transmission of the RF wave and the reception of the reflected electric wave are performed at least twice at different positions. The time interval related to each of the reflected electric waves of the second and subsequent repeats is compared with a time interval related to the reflection of the RF wave to judge an abnormality occurrence direction.

According to an eighth aspect of the present invention, there is provided a method of inspecting an abnormality occurring inside a pipe to be inspected which comprises the steps of transmitting an RF wave having a predetermined frequency from an antenna of a transmitter located inside the pipe, receiving the transmitted RF wave with an antenna of a receiver located at a position spaced apart from the transmitter by a predetermined distance, comparing an intensity of the received RF wave with an intensity of the RF wave transmitted from the transmitter, and judging that an abnormality exists which constricts an inner diameter of the pipe when the amount of attenuation of the received RF wave exceeds a predetermined amount.

In order to achieve the first object, according to a ninth aspect, there is provided an apparatus for inspecting an abnormality occurring inside a pipe to be inspected which includes a transmitter for transmitting an RF wave having a predetermined frequency from an antenna located inside the pipe, a receiver for receiving the transmitted RF wave with an antenna located inside the pipe at a position spaced apart from the transmitter by a predetermined distance, an amplifier for amplifying the received RF wave, a processing unit for comparing an intensity of the received RF wave with an intensity of the transmitted RF wave and calculating an attenuation amount of the received RF wave, a distance input unit for inputting distance data to the processing unit so as to correct the attenuation amount by attenuation due to the distance between the antenna of the transmitter and the antenna of the receiver, and a display unit for displaying the intensity of the received RF wave.

In order to achieve the second object, according to a tenth aspect, there is provided an apparatus for inspecting an abnormality occurring inside a pipe to be inspected which includes a transceiver for transmitting an RF wave having a predetermined frequency inside the pipe and receiving the RF wave reflected by an obstacle existing inside the pipe, and a measuring unit for measuring a time interval between transmission and reception of the RF wave.

As is apparent from the above, according to the present invention an RF wave having a predetermined frequency is transmitted in a pipe to be inspected. An attenuation amount of an RF wave propagating through the pipe, or the time required from the transmission of the RF wave to its reception, is then obtained. The presence of an abnormality, such as a constriction of the inside diameter of the pipe, or an obstacle which clogs it, and the position of the abnormality, are sensed with any one of the two values, thereby easily and accurately determining the state of the pipe inside. In addition, since an RF wave is used, the state of the pipe inside can readily be determined even if the pipe is compoundly curved. Since the inspection distance can be comparatively long, the interior of the pipe can be inspected with a smaller number of inspections each spanning a longer distance.

The above and many other advantages, features and additional objects of the present invention will become manifest to those versed in the art upon making reference to the following detailed description and accompanying drawings in which preferred structural embodiments incorporating the principles of the present invention are shown by way of illustrative example.

DETAILED DESCRIPTION OF THE PREFERRED EMBODIMENTS

The present invention will be described in detail with reference to several preferred examples illustrated in the accompanying drawings.

The first example of a method of inspecting an abnormality occurring inside a pipe according to the present invention, and an example of an apparatus for practicing this method, will be described with reference to FIGS. 1 to 11. Assume that a domestic gas pipe buried underground is to be inspected.

Figure 1:
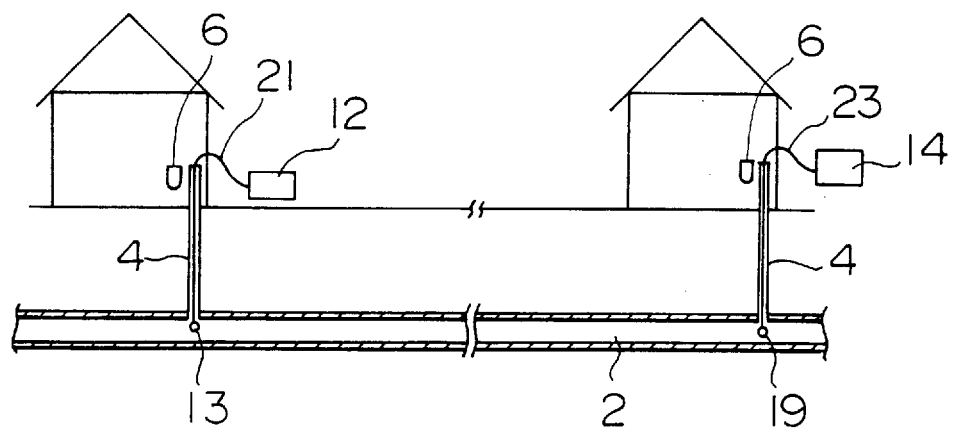
FIG. 1 illustrates a first example of an inspecting method according to the present invention.

The domestic gas pipe includes a trunk gas pipe 2 buried underground, domestic gas pipes 4 branching from the trunk gas pipe 2, and gas-meters 6 which are mounted at the ends of the domestic gas pipes 4 to supply gas for domestic use, as shown in FIG. 1.

Figure 2:
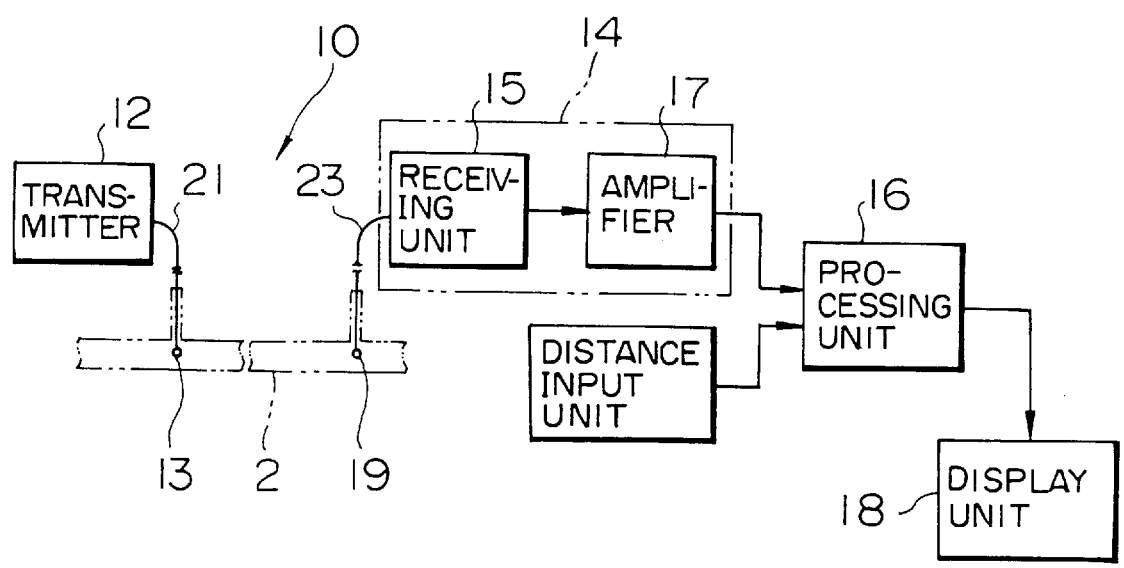
FIG. 2 is a block diagram of an apparatus for performing the inspecting method shown in FIG. 1.

The following description is related to the inspection of the internal state of the trunk gas pipe 2, and FIG. 2 shows an example of an inspecting apparatus for practicing the inspecting method of the first example. An inspecting apparatus 10 comprises a transmitter 12, a receiver 14, a processing unit 16, and a display unit 18. The transmitter 12 can continuously variably transmit an RF wave having a frequency on the order of GHz. A transmission antenna 13 is mounted at the distal end of a lead wire 21. The receiver 14 comprises a receiving unit 15 and an amplifier 17. A reception antenna 19 is mounted at the distal end of a lead wire 23 extending from the receiving unit 15 in the same manner as on the transmitter 12. Upon reception of the RF wave transmitted from the transmitter 12, the corresponding signal is amplified, and the amplified signal is sent to the processing unit 16.

The processing unit 16 inputs an RF wave received by the receiver 14 and compares its intensity to that of the previously input RF wave transmitted by the transmitter 12 to detect the amount of attenuation of the received RF wave. A distance input unit 20 is connected to the processing unit 16. The distance between antennas 13 and 19 is input from the distance input unit 20, and the attenuation amount is changed on the basis of a distance input value. More specifically, only an attenuation amount generated upon propagating the wave through the trunk gas pipe 2 between the antennas 13 and 19 is changed. The changed attenuation amount is sent to the display unit 18, which displays this value.

Inspection procedures will be described below. Two gas-meters 6 which interpose a target portion to be inspected are selected. The domestic gas pipes 4 are disconnected from these gas-meters 6, respectively. The antenna 13 of the transmitter 12 is inserted from an opening of one removed domestic gas pipe 4 and is passed until the antenna 13 reaches the interior of the trunk gas pipe 2. This operation may be performed after or before gas supply is interrupted. If gas supply is not interrupted during the inspection, the openings of the domestic gas pipes 4 are sealed to prevent gas leakage.

The antenna 19 of the receiver 14 is inserted from the opening of the domestic gas pipe 4 corresponding to the other domestic meter 6 until the antenna 19 reaches the interior of the trunk gas pipe 2. In this manner, when the target to be inspected in the trunk gas pipe 2 is between antennas 13 and 19 of the transmitter 12 and the receiver 14, an RF wave having a frequency higher than a value obtained with the equation f=c/1.706 d (where f is a frequency, c is the velocity of light, and d is the inner diameter of a pipe to be inspected) is transmitted from the transmitter 12. For example, if the trunk gas pipe 2 is a 100A pipe, the RF wave has a frequency of 1.67 GHz or more. An RF wave having a frequency equal to or higher than the frequency obtained with the above equation has the characteristic of allowing the RF wave to propagate with minimum attenuation in a pipe having the inner diameter used in the equation.

The RF wave in the predetermined frequency band is transmitted from the transmitter 12 while continuously changing its frequency, and the RF wave propagating through the trunk gas pipe 2 is received by the receiver 14. The received RF wave is sent to the processing unit 16, and the intensity of the received RF wave is compared with the intensity of an RF wave transmitted from the transmitter 12 to detect the amount of attenuation. In addition, correction is performed on the basis of the amount of attenuation caused by the distance between the antennas 13 and 19 which is input from the distance input unit 20. The resultant value is displayed on the display unit 18, and the internal state of the trunk gas pipe 2 is inspected. More specifically, when water, earth, sand and the like enter trunk gas pipe 2 and constrict its interior, an RF wave received by the receiver 14 is attenuated in accordance with the degree of constriction. For this reason, the attenuation of the RF wave obtained by the processing unit 16 is an indication of the extent of clogging inside the trunk gas pipe 2.

Figure 3:
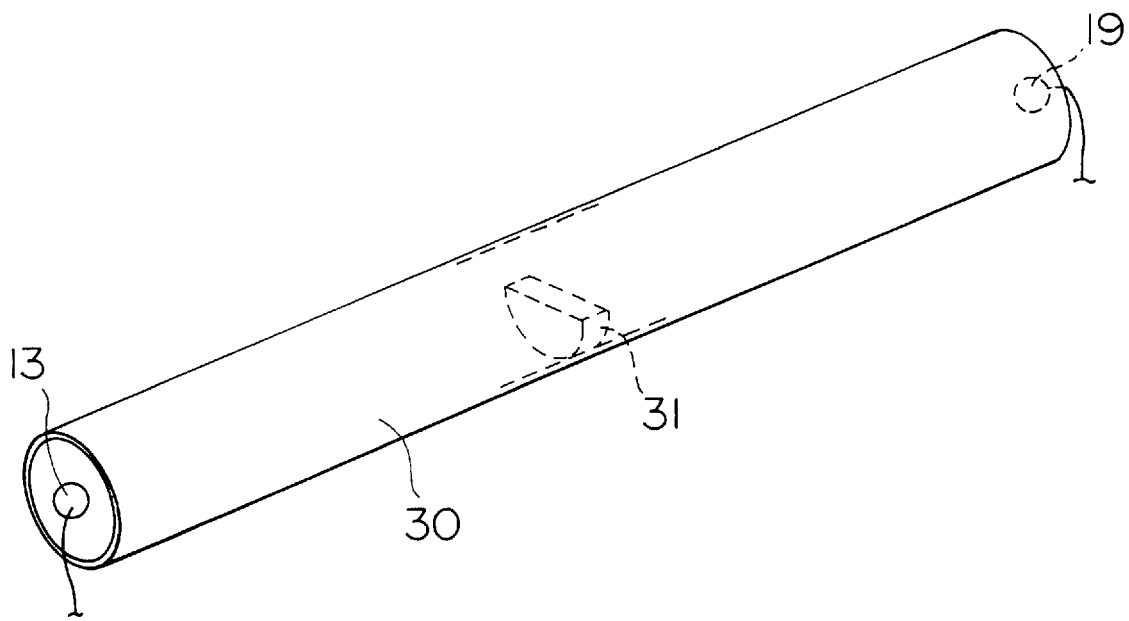
FIG. 3 is a schematic perspective view showing an experimental apparatus using the inspecting method of the present invention.
Figure 4:
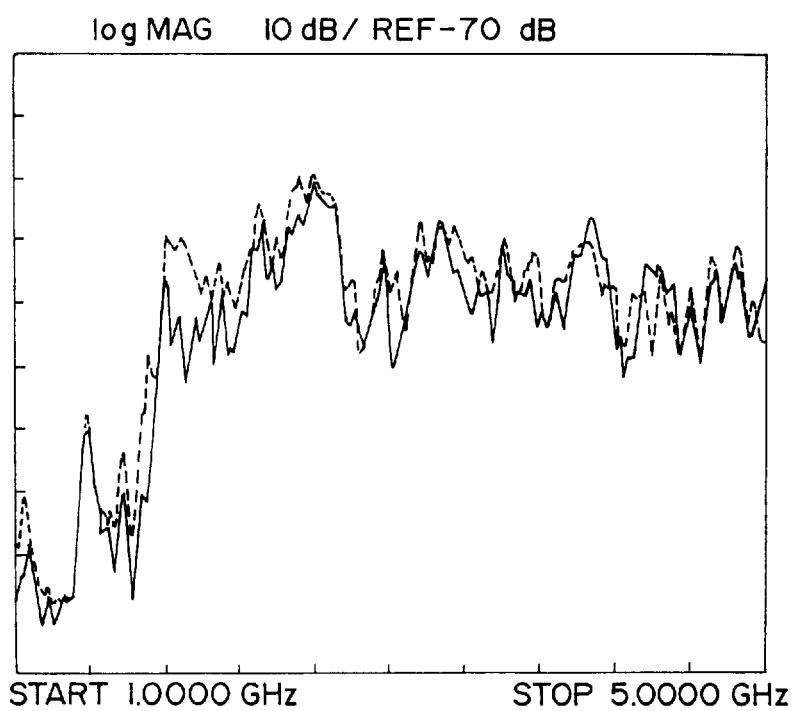
FIG. 4 is a graph showing the results of a comparative experiment and Experiment 1.
Figure 5:
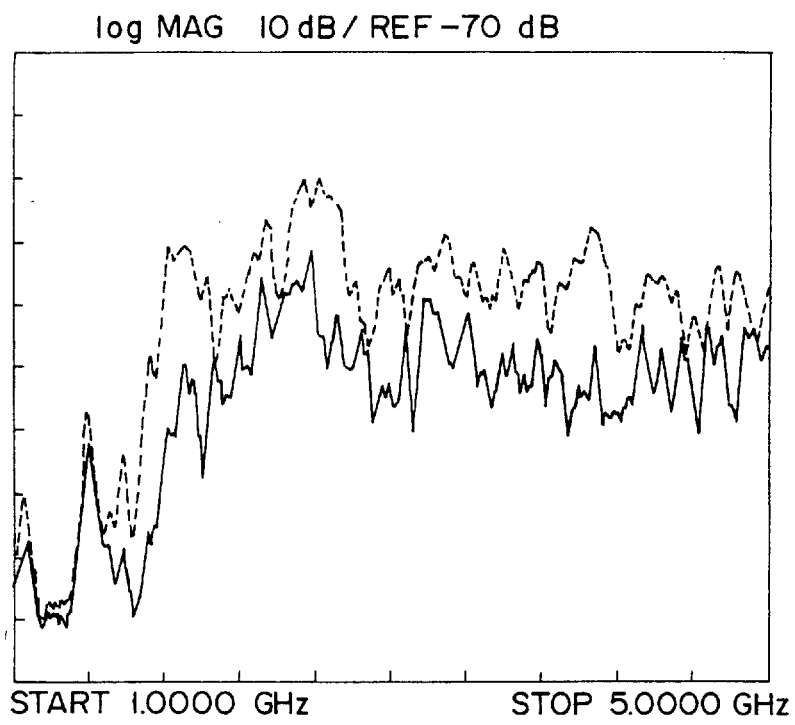
FIG. 5 is a graph showing the results of the comparative experiment and Experiment 2.
Figure 6:
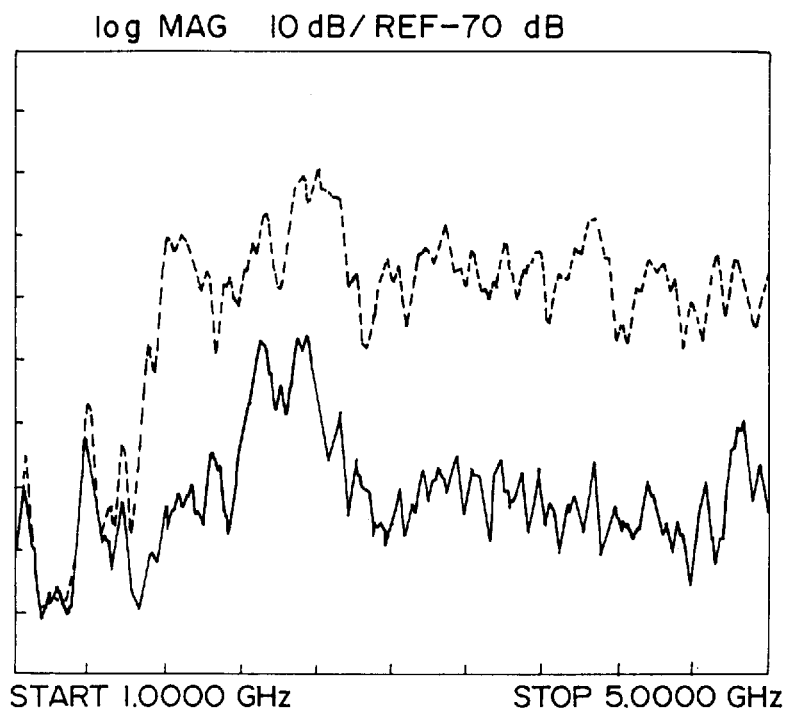
FIG. 6 is a graph showing the results of the comparative experiment and Experiment 3.

Experiments using the above inspecting method will be described below. FIG. 3 shows an experimental apparatus for practicing the present invention.

In this experiment, a gas pipe 30, referred to as a 100A gas pipe having an inner diameter of about 105 mm, was used. The gas pipe 30 had a length of about 150 cm. The antennas 13 and 19 of the transmitter and the receiver were respectively connected to the two ends of the pipe and located slightly inside the pipe. An RF wave having the frequency which continuously changes over the range of 1.0 GHz to 5.0 GHz was transmitted, and an obstacle 31 was placed at the center of the interior of the pipe. The obstacle 31 was a partially notched, circular, thick plate having an outer diameter almost equal to the inner diameter of the gas pipe 30. The shape and area of this notched portion can be varied to change the extent of clogging of the gas pipe 30 by the obstacle. Furthermore, an aluminum foil was wrapped about the surface of the obstacle 31.

More specifically, the following five types of experiments were performed. As a comparative experiment, the obstacle 31 was not located inside the gas pipe 30, an RF wave was transmitted from the transmitter, and the transmitted RF wave was received by the antenna 19 of the receiver opposing the transmitter. In addition, an obstacle 31 having a shape to cover one-half the cross-sectional area of the gas pipe 30 was inserted into the gas pipe, and the antenna 19 received the RF wave in the same manner as in the comparative experiment (Experiment 1). Another obstacle 31 covering two-thirds of the sectional area of the gas pipe 30 was inserted into the pipe, and the antenna 19 received the RF wave in the same manner as in the comparative experiment (Experiment 2). A further obstacle 31 covering the entire cross-sectional area of the gas pipe 30 was inserted into the pipe, and the antenna 19 received the RF wave in the same manner as in the comparative experiment (Experiment 3). Water was then poured inside the gas pipe 30, and the antenna 19 received the RF wave in the same manner as in the comparative experiment (Experiment 4). In Experiment 4, water was poured into a PET resin container having a cross-sectional area equal to that of the gas pipe 30, and the container was inserted into the pipe. The results of Experiments 1 to 4 are shown in FIGS. 4 to 7, and the results of the comparative experiment are represented by dotted lines in the graphs.

Figures 7, 8:
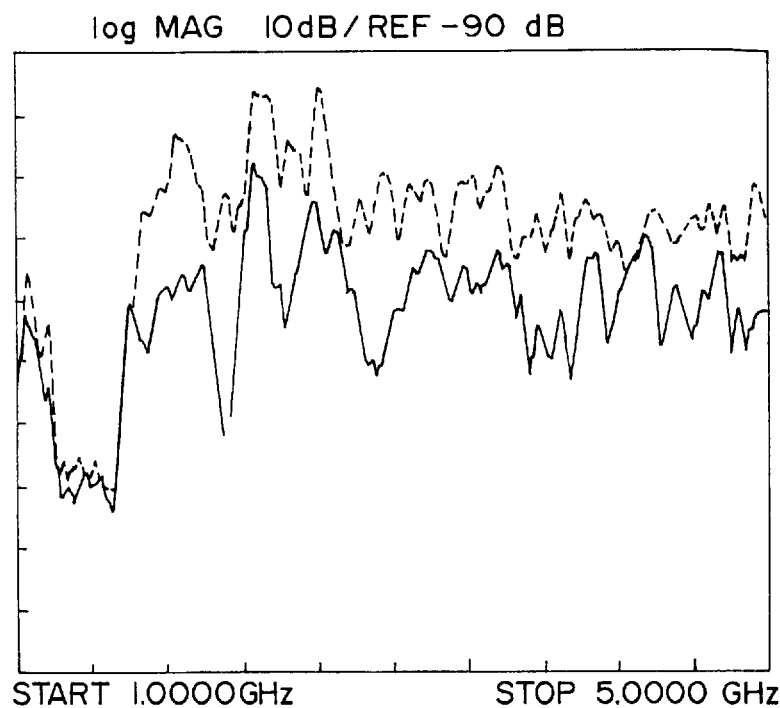
FIG. 7 is a graph showing the results of the comparative experiment and Experiment 4.
FIG. 8 is a table showing the results of Experiment 6.

Experiment 6 was performed under the same conditions as described above except that the frequency was set at 2.5 GHz, and one-third of the gas pipe 30 was closed. The results of Experiment 6 are shown in FIG. 8. From these results, a criterion for judging that a foreign substance exists in the pipe is an attenuation amount of −35 dbm or less.

Figure 9:
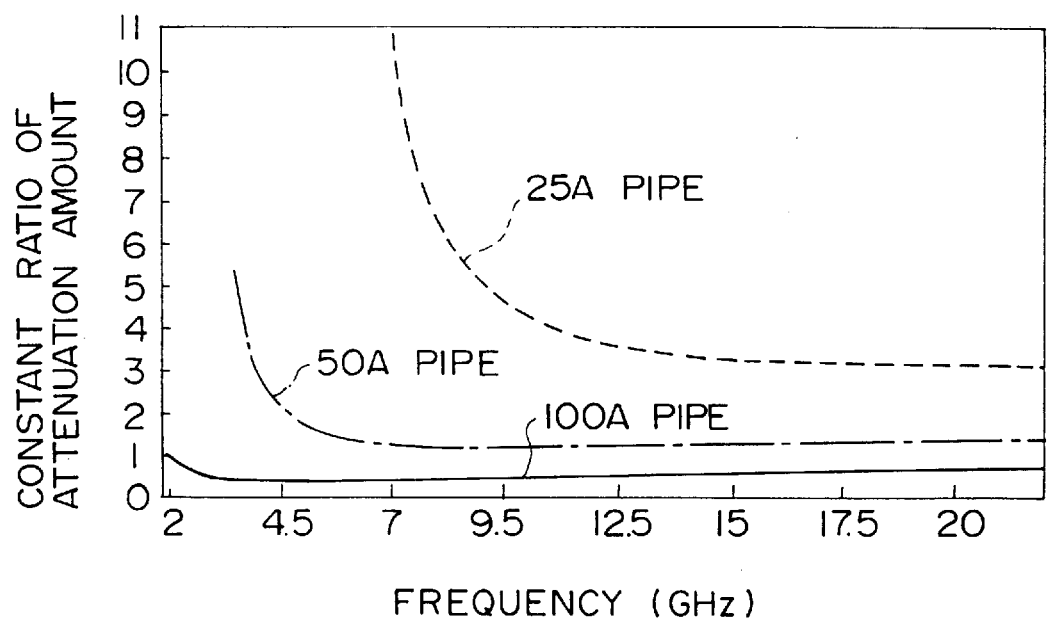
FIG. 9 is a graph showing the constant ratios of attenuation.
Figure 10:
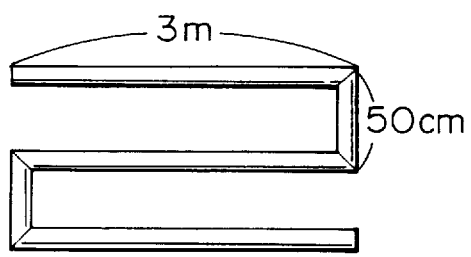
FIG. 10 is a plan view showing a bent pipe used in still another experiment.

Furthermore, FIG. 9 shows attenuation constants. The graph shows an attenuation constant ratio at each frequency when the attenuation constant of the 100A pipe at 2 GHz is set to be 1, and the attenuation constant ratios of the 50A and 25A pipes, respectively. Therefore, when the attenuation constant of the 100A pipe at 2 GHz is 0.4 dB/m, differences in each pipe at the respective frequencies and differences between the attenuation constants in different inner diameters of the pipes can be obtained from FIG. 9, and an attenuation amount for correction is obtained after the attenuation constant is corrected.

Figure 11:
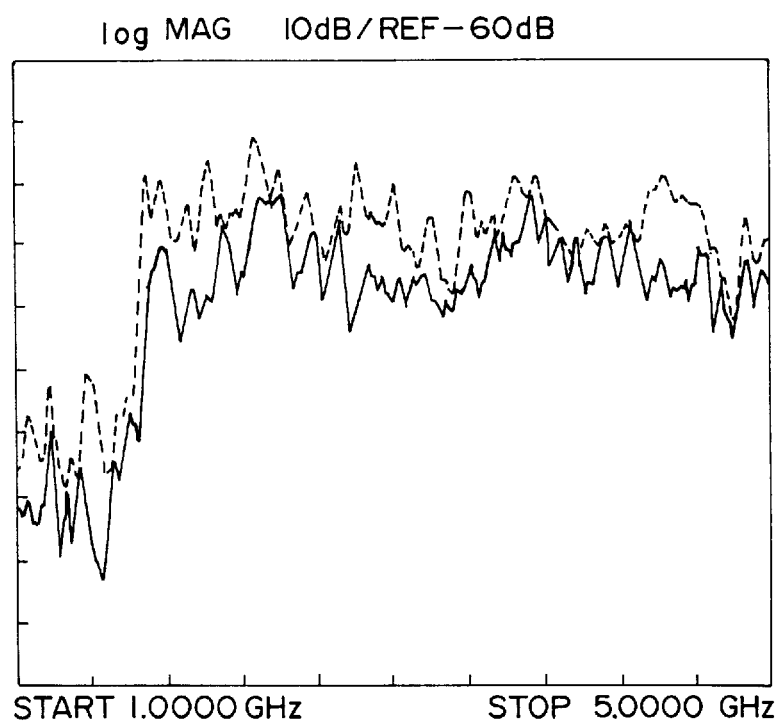
FIG. 11 is a graph showing the results of an experiment performed using the bent pipe shown in FIG. 10.

In a further Experiment 7, a transmitter and a receiver were respectively placed at the two ends of each of a 100A pipe having a length of 1 m, and a bent pipe which is obtained by alternately connecting 100A pipes each having a length of 3 m and 100A pipes each having a length of 50 cm at a right angle, and an RF wave was transmitted and received in each. The results are shown in FIG. 11 (the result of the 100A pipe having a length of 1 m is represented by a dotted line). As the results show, even with a pipe having many bent portions, the attenuation amount of RF wave is relatively small.

As has been described above, according to the first example, each of the antennas 13 and 19 of the transmitter 12 and the receiver 14 is inserted from one end of a corresponding one of the domestic gas pipes 4 at the mounting portions for the spaced-apart two domestic gas-meters 6 and is passed into the trunk gas pipe 2 where the inspection target is. When the attenuation amount of the RF wave transmitted from the transmitter 12 is measured, the extent of clogging of the trunk gas pipe 12 between the transmission antenna 13 and the reception antenna 19 can be accurately determined. In addition, the inspection distance can be increased because an RF wave is used. Thus, a relatively long trunk gas pipe 2 requires fewer inspections to cover its entire length. Even if the trunk gas pipe 2 includes a relatively large number of bends, the RF wave has a small attenuation amount to facilitate accurate inspection.

The above embodiment has exemplified a gas pipe as a target object. However, the inspecting method of the present invention is not limited to use with gas pipes. In addition, the antenna 13 or the like need not be inserted from the connection pipe for the corresponding gas-meter 6.

Figure 12:
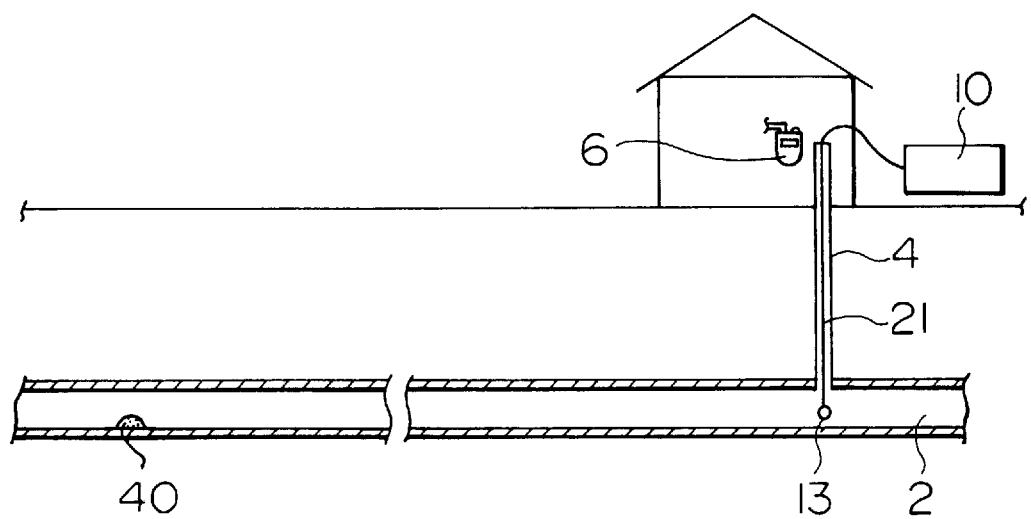
FIG. 12 illustrates a second example of an inspecting method according to the present invention.

The second example of the present invention will be described with reference to FIGS. 12 and 13.

Figure 13:
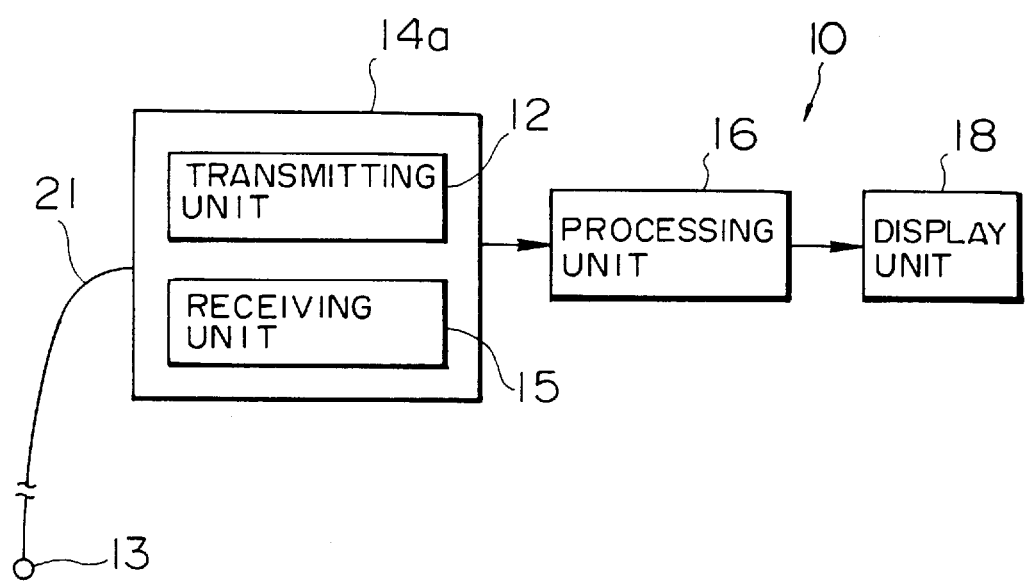
FIG. 13 is a block diagram of an apparatus for performing the inspecting method shown in FIG. 12.

An example of an inspecting apparatus 10 used in the second example is illustrated in FIG. 13. It comprises a transceiver 14a, formed by a combined transmission unit 12 and reception unit 15 for an RF wave, a processing unit 16, and a display unit 18. The transmission unit 12 of the transceiver 14a can transmit an RF wave having a frequency on the order of GHz. A transmission/reception antenna 13 is mounted at the distal end of a lead wire 21 connected to the transceiver 14a. The antenna 13 is also connected to the reception unit 15, and receives an RF wave transmitted from the transmission unit 12 after it has been reflected. The corresponding signal is amplified, and the amplified signal is sent to the processing unit 16.

The processing unit 16 compares the RF wave transmitted from the transmission unit 12 with the RF wave received by the reception unit 15 and measures the time interval between the transmission and reception of the RF wave. The processing unit 16 divides this time interval into one-half and multiplies the resultant value with the velocity of light to calculate the distance to an obstacle. The obtained distance is sent to the display unit 18, and this value is displayed.

Inspection procedures will be described below. A gas-meter 6 near a target to be inspected is selected. A domestic gas pipe 4 is disconnected from the gas-meter 6. The antenna 13 of the transceiver 14a is inserted from an opening of the removed domestic gas pipe 4 and is passed until the antenna 13 reaches the interior of a trunk gas pipe 2. This operation may be performed after or before gas supply is interrupted. If gas supply is not interrupted during the inspection, the opening of the domestic gas pipe 4 is sealed to prevent gas leakage.

In this manner, when the antenna 13 of the transceiver 14a is located near the target portion of the trunk gas pipe 2 to be inspected, an RF wave having a frequency higher than a value obtained with the equation f=c/1.706 d (where f is a frequency, c is the velocity of light, and d is the inner diameter of a pipe to be inspected) is transmitted from the transmitter 12. For example, if the trunk gas pipe 2 is a 100A pipe having an inner diameter of about 105 mm, the RF wave has a frequency of 1.67 GHz or more. The RF wave having a frequency equal to or higher than the frequency obtained with the above equation has the characteristic of allowing the RF wave to propagate with minimum attenuation in a pipe having the inner diameter inserted in the equation.

Immediately after an RF wave having a predetermined frequency is transmitted from the transmission unit 12, the reception unit 15 is set in a receiving state to receive the reflected wave. The reception unit 15 may normally be in its receiving state. The RF wave impinges on an obstacle 40 and is reflected by it, and the reflected RF wave returns through the pipe and is received by receiving unit 15 via the antenna 13. After the received RF wave is amplified, the amplified RF wave is sent to the processing unit 16. The corresponding signals are binarized such that a signal exceeding a threshold level is set to "1", and a signal below the threshold level is set to "0". The resultant value is compared with the RF wave transmitted by the transmission unit 12 to detect the lapse of time between transmission and reception. A distance to the obstacle 40 is calculated from this lapse of time, and the resultant value is displayed on the display unit 18.

When no RF wave is observed, it is judged that no obstacle 40 exists over the length of the pipe over which the RF wave can be transmitted and reflected. For example, assume that the antenna 13 is located at an intermediate position in the pipe, and that the RF wave propagates inside the pipe in both directions. In such a case, if an obstacle 40 is perceived, it cannot be determined in which direction obstacle 40 is located. The antenna 13 is then slightly shifted to inspect the obstacle again. If the distance to the obstacle 40 becomes shorter, it is determined that the obstacle 40 is located on the side to which the antenna 13 has been moved, and if a distance to the obstacle 40 becomes longer, it is determined that the obstacle 40 is located on the opposite side.

As has been described above, according to this embodiment of the present invention, the antenna 13 of the transceiver 14a is inserted from the mounting portion of the domestic gas-meter 6 and passed to the trunk pipe 2 as an inspection target. Then, a reflection time between the transmission of the RF wave from the transmission unit 12 and its reception is measured, thereby accurately determining the distance from the antenna 13 to the obstacle 40. In addition, the inspection distance can be increased because an RF wave is used. A long trunk gas pipe 2 can be inspected with a smaller number of inspection cycles. Even if the trunk gas pipe 2 is intricately bent, the RF wave has a small attenuation amount to facilitate accurate inspection.

The above embodiment has exemplified a gas pipe as an inspection target. However, the inspecting apparatus of the present invention is not limited for use with only gas pipes.

In addition, in the above embodiment, the antenna 13 or the like is inserted from the connection port of the corresponding gas-meter 6. However, insertion of the antenna 13 or the like is not limited thereto. The antenna may be inserted, for example, at another location along the pipe which is accessible.

What is claimed is:

1. A method of inspecting an abnormality occurring inside a pipe to be inspected, comprising the steps of: transmitting a radio wave having a frequency higher than a value obtained with an equation f=c/1.706 d, where f is a frequency, c is the velocity of light, and d is an inner diameter of said pipe, from a stationary antenna of a transmitter located inside said pipe; receiving a radio wave transmitted from said stationary antenna of the transmitter with a stationary antenna of a receiver located inside the pipe at a position longitudinally spaced far from said stationary antenna of said transmitter by a predetermined distance; comparing an intensity of the received radio wave with an intensity of the radio wave transmitted by said transmitter; and determining that the abnormality exists inside the pipe which constricts an inner diameter of said pipe when the intensity of the received radio wave is below a predetermined amount.

2. An apparatus for inspecting an abnormality occurring inside a pipe to be inspected, comprising: a transmitter for generating a radio wave having a frequency higher than a value obtained with an equation f=c/1.706 d, where f is a frequency, c is the velocity of light, and d is an inner diameter of said pipe; a stationary transmitting antenna located inside said pipe and coupled to the transmitter for transmitting the radio wave along the inside of the pipe in the longitudinal direction; a receiver for receiving the radio wave transmitted from said transmitting antenna through a stationary receiving antenna located inside the pipe at a position longitudinally spaced far from said transmitting antenna by a predetermined distance; a processing unit for comparing an intensity of the received radio wave with an intensity of the transmitted radio wave and for calculating an attenuation amount by which the intensity of the received radio wave was attenuated relative to the intensity of the transmitted radio wave; a distance input unit coupled to said processing unit for inputting data to said processing unit reflecting the predetermined distance between the antennas so as to correct said attenuation amount by a factor which is a function of the distance between said antennas; and a display unit for displaying an intensity of the received attenuated radio wave.

3. A method of inspecting a pipe for an abnormality occurring inside the pipe, the method comprising the steps of:

transmitting a radio wave having a predetermined frequency from a first stationary antenna located at a first predetermined position inside the pipe;

receiving the radio wave with a second stationary antenna located at a second predetermined location inside the pipe, the second predetermined location being longitudinally displaced along the pipe from the first predetermined location; and evaluating a characteristic of the radio wave after the radio wave is received to determine if an abnormality is present within the pipe.

4. The method of claim 3 wherein the step of evaluating a characteristic of the radio wave comprises:

determining an intensity of the radio wave after the radio wave is received;

determining an attenuation amount by comparing the intensity of the radio wave after the radio wave is received with an intensity of the radio wave when the radio wave is transmitted; and deciding that an abnormality exists within the pipe that constricts an inner diameter of the pipe when the attenuation amount exceeds a predetermined value.

5. A method according to claim 4 wherein the attenuation amount is corrected by an attenuation correction factor that is based on the distance between the second predetermined location and the first predetermined location.

\* \* \* \* \*